United States Patent [19]
Liu et al.

[11] Patent Number: 6,136,820
[45] Date of Patent: Oct. 24, 2000

[54] ISOLATION OF CASTANOSPERMINE AND ITS USE AS AN ANTIDIABETIC AGENT

[75] Inventors: Paul S. Liu; Barry L. Rhinehart, both of Indianapolis, Ind.

[73] Assignee: Merrell Pharmaceuticals Inc., Bridgewater, N.J.

[21] Appl. No.: 07/622,305

[22] Filed: Dec. 5, 1990

Related U.S. Application Data

[63] Continuation of application No. 07/501,976, Mar. 29, 1990, abandoned, which is a continuation of application No. 07/356,666, May 23, 1989, abandoned, which is a continuation of application No. 07/228,790, Aug. 4, 1988, abandoned, which is a continuation of application No. 07/728,127, May 24, 1985, abandoned.

[51] Int. Cl.$^7$ ................................................ A61K 31/435
[52] U.S. Cl. .......................... 514/299; 514/413; 514/866; 546/183
[58] Field of Search .................................... 514/413, 866, 514/299; 546/183

[56] References Cited

U.S. PATENT DOCUMENTS 4,312,872  1/1982  Junge et al. ............................ 514/866

OTHER PUBLICATIONS

Schlesinger, et al., J; Biol. Chem., 259 (12) 7591–7601, 1984.
Saul, et al., Fed Proc., 42 (7) 2083 Abstr. 1908, 1983.
Saul, et al., Arch Biochem Brophys., 221 (2), 593–597, 1983.
Saul, et al. Arch Biochem Biophys. 230 (2) 668–675, 1984.
Hohenschutz, et al., Phyls chem., 20 (4), 811–814, 1981.
Hori et al Arch. Biochem. Biophys., 228 (2), 525–533, 1984.
Pan, et al., Biochem. 22 (16), 3975–3984, 1983.
Pan et al, Fed. Proc., 42 (7), 2084, Abstr. 1909, 1983.
Chabsts. 95:204245e 1981.
Elbein, et al., J. Backeriol., 160 (1), 67–75, 1984.
Ghidoni, et al., Fed Proc. 43 (3), 618 Abstr. 1946, 184.
Bernotas, et al., Tetra Hevron Letters 25(2): 165–168, 1984.
Saul et al Fed Proc. 42(7):2083 Abst. 1908, 1983.
Saul et al., PNAS 82: 93–97, 1985.

*Primary Examiner*—Francisco Prats
*Attorney, Agent, or Firm*—Stephen L. Nesbitt; Balaram Gupta

[57] ABSTRACT

A method for inhibiting the formation of glucose by the administration of castanospermine is described herein. In addition, a new process for the isolation of castanospermine from *Castanospermum australe* is also described.

4 Claims, No Drawings

ISOLATION OF CASTANOSPERMINE AND ITS USE AS AN ANTIDIABETIC AGENT

CROSS-REFERENCE TO RELATED APPLICATION

This is a continuation of application Ser. No. 07/501,976, filed Mar. 29, 1990, now abandoned which is a continuation of application Ser. No. 07/356,666, filed May 23, 1989, now abandoned, which is a continuation of application Ser. No. 07/228,790, filed Aug. 4, 1988, now abandoned, which is a continuation of application Ser. No. 07/728,127, filed May 24, 1985, now abandoned.

BACKGROUND OF THE INVENTION

Castanospermine is an alkaloid having the following formula:

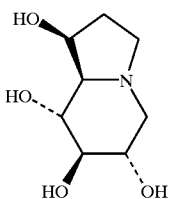

Systematically, this compound is named (1S,6S,7R,8R,8aR)-1,6,7,8-tetrahydroxyindolizidine.

The isolation of of this compound from Castanospermum australe has been described by L. D. Hohenshutz, et al., *Phytochemistry*, 20, 811 (1981). The procedure involves a tedious extraction and a subsequent washing with pyridine and only small quantities of the desired product are obtained. R. C. Bernotas, et al., *Tetrahedron Letters*, 25, 165 (1984) obtained castanospermine by total synthesis and thereby established the absolute configuration of the compound.

Several publications have appeared which describe castanospermine as an inhibitor of a number of plant enzymes. See Y. T. Pan, et al., *Biochemistry*, 22, 3975 (1983); R. Saul, et al., *Archives of Biochemistry and Biophysics*, 221, 593 (1983); R. Saul, et al., Archives of Biochemistry and Biophysics, 230, 668 (1984). More recently, Saul et al., *Proc. Nat'l. Acad. Sci. USA*, 82, 93 (1985) have indicated that castanospermine inhibits intestinal glycosidases (i.e., maltase and sucrase) in rats when administered by injection and that diarrhea and high levels of intestinal bacterial flora were observed when high doses were administered. However, they gave no indication that castanospermine would be useful for any purposes as a result of these facts.

DESCRIPTION OF THE INVENTION

It has now been found that castanospermine possesses digestive enzyme inhibitory properties and thus can be used as an antidiabetic agent and as an inhibitor of increased lipid biosynthesis. Thus, when carbohydrate is ingested either as glucose or in a form such as maltose, sucrose or starch in food or drink, the blood glucose level rises to elevated concentrations. In healthy subjects, this hyperglycemic state quickly returns to normal, the glucose in the blood being rapidly metabolized and stored and/or utilized by the organism. In diabetes mellitus, however, the glucose tolerance of the patient is lowered and the abnormally high blood sugar levels which develop remain elevated for prolonged periods of time. A similar response to that seen in man can also be observed in other animals, including livestock, poultry, pet animals and laboratory animals. Such a condition can be described as postprandial hyperglycemia. One method for treating such a condition would be by administration of some substance which would prevent the conversion of complex sugars to glucose and thus prevent the development of the excessive glucose levels. In the present invention, it has been found that, where the high levels of glucose are a result of the hydrolysis of complex sugars, administration of castanospermine inhibits the initial formation of glucose in the blood and thus makes it possible to avoid the problems which would be associated with prolonged high levels of blood sugar.

Equivalent to castanospermine for the purposes of this invention are the salts of castanospermine with pharmaceutically acceptable acids and, particularly, with inorganic acids such as hydrochloric acid, hydrobromic acid, sulfuric acid and phosphoric acid; and with organic acids such as acetic acid, propionic acid, methanesulfonic acid and p-toluenesulfonic acid.

The mechanism whereby the above result is achieved is the following although the utility described above should not be limited by the precise details of this mechanism. Enzymes which catalyze the hydrolysis of complex carbohydrates convert non-absorbable carbohydrate into absorbable sugars. The rapid action of these enzymes leads to acute and undesirable elevations in blood glucose in diabetes. The compounds of the present invention are potent inhibitors of these enzymes and, when co-administered with a carbohydrate meal, they prevent harmful hyperglycemic excursions of this type.

This inhibition of the formation of glucose can be useful in other ways too. Thus, the carbohydrates ingested by an organism appear in the form of glucose and are metabolized into lipids such as triglycerides, cholesterol, phospholipids and the like. Too large a carbohydrate intake results in increased biosynthesis of lipids, causing hyperlipemia and excessive accumulation of lipids, both in adipose tissue and in other systems in the organism which can lead to obesity, atherosclerosis, myocardial infarction and other kinds of heart diseases. The inhibition of the formation of glucose accomplished by castanospermine would thus be useful in the control of these other conditions.

In addition, the present invention is directed to a new process for the isolation of castanospermine from *Castanospermum australe* by a procedure that avoids the tedious extraction procedure and the use of the obnoxious solvent pyridine as described in the published procedure mentioned earlier while providing the desired product in greatly improved overall yields. Details of this procedure are set forth in the example.

The following test procedures can be used to demonstrate the activity of castanospermine.

Inhibitory Action Against Increase of Blood Glucose in Sucrose-Administered Mice Male ICR-swiss mice with body weight of 25–35 g were fasted overnight. Sucrose was administered orally by gavage at a dose of 2 g/kg 15 minutes after the similar administration of castanospermine at doses of 0.125 to 60 mg/kg. Animals were sacrificed at 30 minutes after sucrose administration and blood glucose levels were measured by a method using glucose dehydrogenase. The results are shown in Table 1 below. The increase in glucose in the blood could be significantly inhibited by administering castanospermine at a dose of 0.125 mg/kg or higher.

TABLE 1

| Dose of Castanospermine | Number of Mice Tested | Blood Glucose Concentration (mg %) at 30 Min. After Sucrose |
|---|---|---|
| 0 mg/kg | 8 | 205 |
| 0.125 | 4 | 159 |
| 0.25 | 4 | 167 |
| 0.5 | 4 | 153 |
| 1.0 | 4 | 146 |
| 2.0 | 4 | 116 |
| Blank | 4 | 107 |

(Blank: 0.5% methocel alone was administered.)

Inhibitory Action Against Increase of Blood Glucose in Starch-Administrated Mice Male ICR-Swiss mice with body weight of 25–35 g were fasted overnight. Starch was administered orally by gavage at a dose of 1 g/kg 15 minutes after the similar administration of castanospermine at doses of 1.9 to 60 mg/kg. Animals were sacrificed at 45 minutes after starch administration and blood glucose levels were measured by a method using glucose dehydrogenase. The results are shown in Table 2 below. The increase in glucose in the blood could be significantly inhibited by administering castanospermine at a dose of 3.8 mg/kg or higher.

TABLE 2

| Dose of the Compound of This Invention | Number of Mice Tested | Blood Glucose Concentration (mg %) at 45 min. After Starch |
|---|---|---|
| 0 mg/kg | 8 | 126 |
| 1.9 | 3 | 139 |
| 3.8 | 4 | 83 |
| 7.5 | 4 | 85 |
| Blank | 4 | 72 |

(Blank: 0.5% methocel alone was administered.)

In practicing the method of this invention, an amount of castanospermine effective to inhibit postprandial hyperglycemia is administered to a mammal in need thereof by a suitable route. For the purposes of this invention, oral administration is preferred.

The effective amount of the compound, that is, the amount sufficient to inhibit postprandial hyperglycemia, depends on various factors such as the size, type and age of the animal to be treated, the particular compound or pharmaceutically acceptable salt employed, the frequency of administration, the severity of the condition and the time of administration. Generally speaking, the compounds would be administered orally at a dose of 10 mg to 500 mg at mealtime, with a dose of 40 mg to 200 mg being preferred. More specifically, the present compounds would be administered to humans in single unit doses (individual capsules) containing 50 mg of active ingredient with the material being administered three times a day at mealtime.

In practicing the method of this invention, the active ingredient can be incorporated in a composition comprising a pharmaceutical carrier and from about 5 to about 90 percent by weight of castanospermine or a pharmaceutically-acceptable salt thereof. The term "pharmaceutical carrier" refers to known pharmaceutical excipients useful in formulating pharmaceutically active compounds for internal administration to animals, and which are substantially non- toxic and non-sensitizing under conditions of use. The compositions can be prepared by known techniques for the preparation of tablets, capsules, elixirs, syrups, emulsions, dispersions and wettable and effervescent powders, and can contain suitable excipients known to be useful in the preparation of the particular type of composition desired. Suitable pharmaceutical carriers and formulation techniques are found in standard texts, such as *Remington's Pharmaceutical Sciences*, Mack Publishing Company, Easton, Pa.

The following example is presented to illustrate the present invention. However, it should not be construed as limiting it in any way.

EXAMPLE 1

Commercially available mature seeds of *Castanospermum australe* (300 g, wet weight) were ground and continuously extracted for 24 hours in a Soxhlet apparatus with 1.0 l of a 3:7 (v/v) mixture of water and 2-propanol. The extract was concentrated in vacuo to a final volume of 250 ml and was filtered. After extraction with petroleum ether (10×100 ml), the aqueous extract was subjected to column chromatography with Dowex 50W-X4 (H+) ion-exchange resin (2.5 cm×32 cm). The column was washed with distilled water (200 ml) and the desired alkaloid was eluted with 400 ml of 2 N aqueous ammonium hydroxide. The basic eluate was concentrated in vacuo to 125 ml and applied to another column containing Dowex 1-X4(OH−) ion-exchange resin (2.5 cm×20 cm). The column was eluted with 125 ml of water and the eluate was concentrated to a final volume of 30 ml. Trituration of the concentrate with 300 ml of acetone yielded 3.5 g of castanospermine as colorless crystals (1.2%, calculation on the basis of the weight of fresh seeds). The isolated crystals had the following physical properties:

mp: 212–225° C.

Elemental analysis: Found: C, 50.53%; H, 8.04%; N, 7.26%. Calc for $C_8H_{15}NO_4$: C, 50.79%; H, 7.94%; N, 7.41%.

Optical rotation=$[\alpha]_D^{25}$+75.5° (c 1.72, $H_2O$)

Mass Spectral Data: 190 ($MH^+$), 172 ($MH^+$-$H_2O$).

What is claimed is:

1. A method for treating diabetes in mammals which comprises administering an effective amount of castanospermine.

2. A method for treating postprandial hyperglycemia in diabetic individuals which comprises administering an effective amount of castanospermine.

3. A method for inhibiting carbohydrate absorption in mammals which comprises administering an effective amount of castanospermine.

4. A process for obtaining castanospermine from the seeds of Castanospermum australe which comprises:

(a) extracting the ground seeds with about a 3:7 (v/v) mixture of water and 2-propanol;

(b) washing the extract with petroleum ether;

(c) chromatographing the solution on an acid resin with elution with ammonium hydroxide;

(d) rechromatographing the eluate on a basic resin with elution with water; and (e) concentration of the aqueous eluate to about 24% of the original volume followed by trituration with acetone to give castanospermine.

* * * * *